United States Patent [19]

White

[11] Patent Number: 5,063,941

[45] Date of Patent: Nov. 12, 1991

[54] APPARATUS FOR REDUCING THE OCCURRENCE OF SHOULDER DISLOCATION SUBLUXATION DURING ATHLETIC ACTIVITY

[76] Inventor: Christopher A. White, 2323 W. Dunlap Ave., #211, Phoenix, Ariz. 85021

[21] Appl. No.: 618,062

[22] Filed: Nov. 26, 1990

[51] Int. Cl.⁵ .................. A61B 19/00; A61F 5/37; A61F 5/02

[52] U.S. Cl. .................... 128/869; 128/876; 2/45

[58] Field of Search ............... 128/869, 875, 876, 94, 128/165, 77, 78, 95.1; 2/44, 45

[56] References Cited

U.S. PATENT DOCUMENTS

| | | | |
|---|---|---|---|
| 3,906,944 | 9/1975 | Christen | 2/45 |
| 3,970,316 | 7/1976 | Westmoreland, Jr. | 128/876 |
| 4,396,013 | 8/1983 | Hasslinger | 128/876 |
| 4,476,859 | 10/1984 | Kloepfer | 128/94 |
| 4,598,703 | 7/1986 | Lindemann | 128/94 |
| 4,699,132 | 10/1987 | Carville | 128/876 |
| 4,788,941 | 12/1988 | Villeneuve | 128/876 |
| 4,862,878 | 9/1989 | Davison | 2/45 |
| 4,872,216 | 10/1989 | Wingo, Jr. | 2/45 |
| 4,878,490 | 11/1989 | Scott | 128/165 |
| 4,964,401 | 10/1990 | Taigen | 128/876 |

Primary Examiner—Robert A. Hafer
Assistant Examiner—Michael Brown
Attorney, Agent, or Firm—Joseph H. Roediger

[57] ABSTRACT

An athletic brace to be worn with conventional shoulder pads for reducing the chance of subluxation of the shoulder which includes a wide elastic member that is internally wrapped about the upper arm and brought across the chest for attachment to the front of the shoulder pads. The elastic member tends to limit both abduction and external rotation of the upper arm of the user thereby reducing the chance of the athlete reaching the point that tends to stress the glenohumeral joint to the point of subluxation or dislocation.

5 Claims, 2 Drawing Sheets

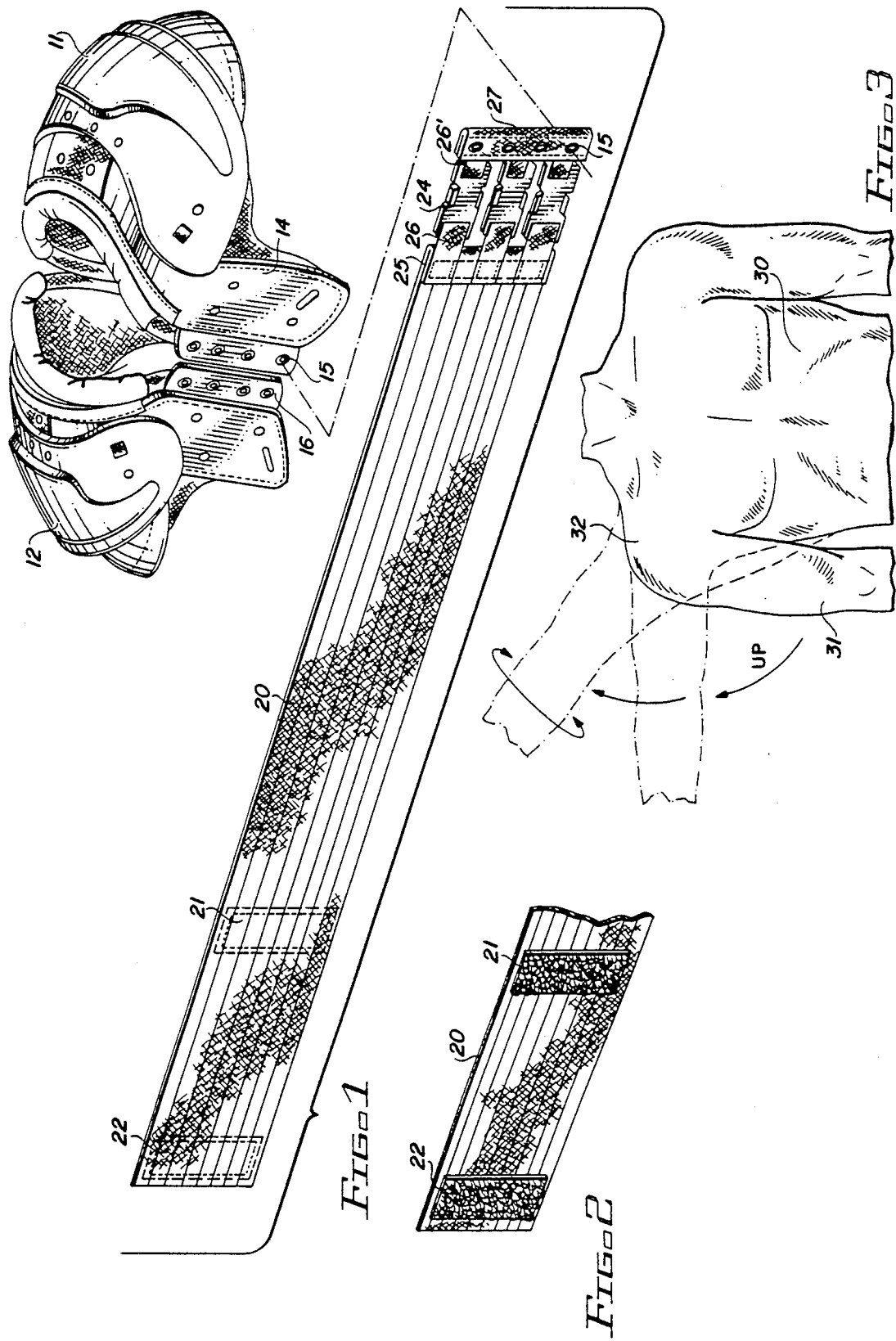

APPARATUS FOR REDUCING THE OCCURRENCE OF SHOULDER DISLOCATION SUBLUXATION DURING ATHLETIC ACTIVITY

BACKGROUND OF THE INVENTION

This invention relates to apparatus for reducing the likelihood of shoulder dislocations or subluxations occuring during athletic activity and, in particular is directed to apparatus to be worn by an athlete equipped with a standard shoulder pad assembly.

In athletic endeavors, the human body is frequently called on to perform certain motions which are not always those with which the musculo-skeletal structure of the body is comfortable. These motions, when repeatedly performed can result in a weakening of the supporting structure surrounding the joint. When a difficult motion is undertaken to an extreme, the joint undergoes a full dislocation. This situation requires a reduction of the joint to restore it to its normal condition. Each time a joint undergoes a full dislocation, the easier it is to have the situation repeat itself. This overall weakening also takes place in the case of partial dislocations where the received bone partially leaves the socket and thereafter returns to the proper position.

While certain joints in the human body are characterized by a deep socket, for example the socket formed in the pelvic bone to receive the head of the femur, there are other joints of the body which are designed for mobility rather than stability. These joints are characterized by relatively shallow socket. One such joint is the shoulder wherein the shallow socket (glenoid fossa) of the scapula receives the head of the humerus or upper arm bone. In athletics, this type of shallow-socket joint is frequently subjected to a motion, which coupled with an external force applied by either a competitor or contact with the ground, results in a partial dislocation or subluxation of the joint.

In the shallow glenohumeral shoulder joint, the mechanism of injury is typically an external rotation of the arm coupled with abduction or movement away from the body by the arm. The shoulder joint need not undergo a full dislocation, but often suffers a partial dislocation where the humerus or arm bone slides part way out of the joint and then moves back into place. As it is repeated, the tendency for it to occur again is greatly increased.

In contact sports such as football and hockey, the participants are equipped with a shoulder pad assembly. These pads cushion impact, but do little or nothing to prevent partial dislocations or subluxations of the shoulder. Consequently, athletes may have their upper torso wrapped with an elastic bandage prior to "putting on the pads." The Shoulder Spica is a well-known wrap that has been used to support the shoulder joint while still permitting use of the arm. The wrap is characterized by wrapping the upper arm and then taking the free end thereof across the chest, under the opposite arm, and behind the back. Three or more upper torso wraps are taken about the chest and back and down the upper arm. The free end is taped which decreases its effectiveness during an athletic workout or game since the wrap tends to loosen with use. Furthermore, the bulkiness of the wrap tends to reduce the field of other motions frequently limiting overall performance. To change the wrap is time-consuming. It requires the over-lying equipment to be removed since no adjustment can be made to the player without repeating the wrapping process.

As a substitute for the Shoulder Spica wrap, mechanical shoulder braces have been designed to assist football players in preventing shoulder subluxation. The braces provide motion inhibiting results when strapped to the torso. Hinged joints of the brace control the movement of the shoulder. These braces are cumbersome and quite expensive. Generally, they are beyond the budgetary abilities of most schools. Furthermore, the range of motion limitations of the brace provide freedom of movement up to the limit with no indication provided to the wearer of when the limit is about to be reached, i.e. no proprioceptive feedback is provided to the wearer. Consequently, the effectiveness of the athlete is reduced when the limit is abruptly reached.

A substitute for the mechanical brace with its hinged joint is the use of a fabric vest and attached half sleeve. Straps across the back and chest are used as stops to limit abduction while the cuff or half-sleeve on the upper arm serve to maintain the combination in position on the torso. The vest-sleeve combination establish limits to abductive movements, i.e. movements away from the central axis of the body, but does not provide any significant control of arm rotation. As a result, severe external rotation of the humerus in relation to the scapula can occur and subluxation is still a cause for concern.

Any device worn to reduce the chance of subluxation of the shoulder requires that resistance to external rotation and abduction be provided but to enhance the effectiveness to the wearer requires that the athlete be able to sense when the limits are being reached. An athlete sensing that he is approaching a limitation on permissible movement can alter his other movements so as to achieve his performance goal. The use of rigid confining harnesses alone or in combination with the fixed length tether of the fabric vest do establish a limit to movement, but fail to provide the athlete with notice that he is about to reach his limit. Without warning of the limit, hockey and lacrosse players raising their stick, or the football receiver extending his arms for the football do not have sufficient time to react and adjust. Thus, the existing orthotic devices decrease performance levels of the wearers.

Accordingly, an object of the present invention is the provision of an improved shoulder brace to reduce the possibility of subluxation. The invention is designed to indicate to the wearer when abduction and external rotation are approaching the limit for this individual so that overall movement can be adjusted to compensate. In addition, the present athletic brace is applied in combination with the conventional shoulder pad assembly when the assembly is in place. Consequently, individual adjustment can be made without requiring the wearer to shed pads and all.

SUMMARY OF THE INVENTION

The present invention is concerned with an athletic brace to be used in combination with a shoulder pad assembly in order to reduce the possibility of a shoulder subluxation while facilitating movement of the upper arm during athletic activities. In particular, the athletic shoulder brace includes an elongated elastic member to be wrapped about the upper arm of the wearer. The elastic member is similar to the elastic wrap utilized by athletic trainers in providing joint support. The elastic member has first and second ends with an engaging means affixed to the member proximate to its first end.

When the elongated elastic member is wrapped about upper arm of the wearer, the engaging means which may be an insert of hooked material, such as that used in the hook and eye fasteners widely used in clothing and containers, engages the adjacent surface of the elastic member to provide a secure initial wrap about the upper arm. The elastic member is further wrapped about the upper arm in an internal wrap in which the first end is brought underneath the arm and then around the back of the arm and over it. The free or second end extends toward the center of the chest.

The second end of the elastic member is provided with attachment means which can be secured to the conventional athletic shoulder pad assembly at a location inwardly spaced from the shoulder. Typically, the attachment means is interlaced using the lashing provided at the front portion of the shoulder pad assembly. The wrapping of the first end about the upper arm then results in a portion of the elastic member extending across the adjacent portion of the chest of the wearer. Since the second end is attached to the shoulder pad assembly, an abduction movement of the upper arm encounters increasing resistance as the elastic member is subjected to tension. In addition, external rotation, i.e. away from the body, of the arm also encounters the increasing opposing force due to tension of the elastic member.

The limits on combined abduction and rotational movement of the upper arm are established when the wrap is made about the upper arm of the wearer. Since the member is elastic, the wearer feels the forces exerted thereby in opposition to his proposed movement. Thus, the wearer is continually made aware of the fact that he is approaching a limitation to his permitted movement well before reaching the point where subluxation of the shoulder is a distinct possibility, should he continue movement of this type. Thus, the athlete engaged in competitive activity can make adjustment for the fact that he is about to encounter a limit to his movement and alter his position or body attitude accordingly. The prospect of the receiver of the football extending his arms and having movement toward the path of the ball abruptly limited without warning is not present.

Furthermore, the placement of the present invention on the wearer takes place after he has been outfitted with all the undergarments and paddings, but just prior to the placement of the identifying shirt which constitutes his outer layer. Adjustments can be affected merely by removing the outer garment from the player and rewrapping the upper arm to adjust the tension of the elastic member when the arm is not extended.

Further features and advantages of the invention will become more readily apparent from the following description of a particular embodiment when viewed in conjunction with the accompanying drawings.

BRIEF DESCRIPTION OF THE DRAWINGS

FIG. 1 is a view in perspective showing a shoulder pad assembly and the subject matter of the invention when detached therefrom.

FIG. 2 is a partial view in perspective showing the engaging means affixed proximate the first end.

FIG. 3 is a partial front view of the human torso illustrating the movements to be controlled.

DESCRIPTION OF THE PREFERRED EMBODIMENT

Figure 4A:
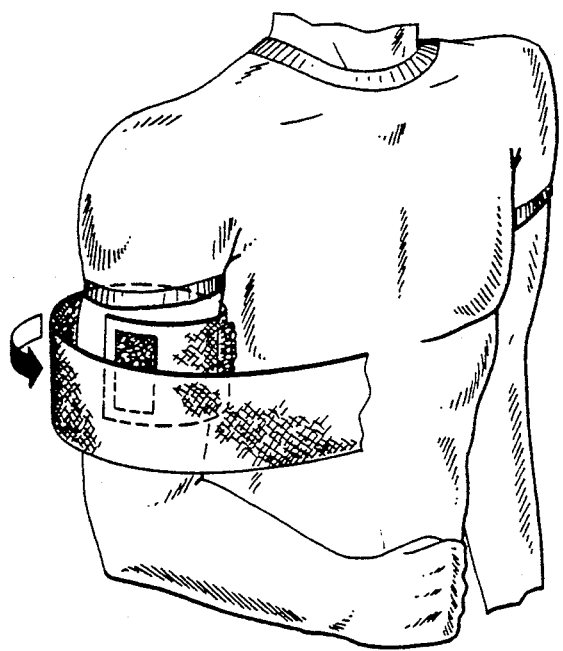
FIGS. 4(a) and 4(b) show the wrapping of the elastic member about the upper arm of the wearer.

Referring now to FIG. 1, a typical shoulder pad assembly 11 is shown without the lashing that secures the frontal protectors 14 to one another. In use, the assembly is slipped over the head of the wearer so that the protective extensions 12 reside on and over the shoulders of the wearer. The frontal protectors 14 extend downwardly providing a degree of protection for the clavicle. Each frontal protector is provided with a tab section 16 containing a plurality of spaced grommets 15. When positioned to be comfortable, the lashing is drawn tight and tied. Typically, the lashing is never removed from the grommets after use, but is merely loosened to enable the wearer to remove the assembly over his head.

The athletic brace to be worn in combination with the shoulder pad assembly 11 is shown in FIG. 1 in an extended position. The brace comprises an elongated elastic member 20 having opposing ends. The elastic member has a free end which is provided with a first engaging means 22 and a second engaging means 21 spaced inwardly therefrom. As will later be described, this portion of the elastic member 20 is wrapped about the upper arm of the wearer.

The opposing end of the elastic member is provided with a plurality of spaced grommets 15 at second end 27. The grommets are spaced so that they will substantially register with grommets 15 on the tab 16 of the shoulder pad assembly. In practice, the lashing used for the shoulder pad assembly secures the second end 27 to the adjacent tab 16. The second end 27 is secured by fabric extensions 26 which are coupled to a plurality of individual release means 24. The release means are detachable into male and female components by finger pressure exerted on their side. The other end of the release means is affixed by fabric extensions 26 to a flap 25 which is folded back upon the elastic member to provide a double thickness termination.

The elongated elastic member may be fabricated from the elastic wrap material used by athletic trainers today so that it has elasticity in all directions and is capable of being conformably wrapped on the upper arm of the wearer.

As shown in FIG. 2, the spaced engaging means 21 and 22 are formed on the same side of the elastic member with one located fairly close to the free end, and the other inwardly spaced therefrom. Since many of the elastic wraps are made from a ribbed fabric that has a rough surface that exposes threads, the engaging means in the embodiment shown are patches of hook material such as used in the common hook-eye fasteners found in multiple uses with containers, clothing and footwear and the like. It is recognized that other fasteners can be used if desired. The location of the patches forming the engaging means is not particularly critical since they are designed to engage the adjacent surface of the portion of the elastic member and thus both are placed on the same surface of the elastic member.

Figure 4B:
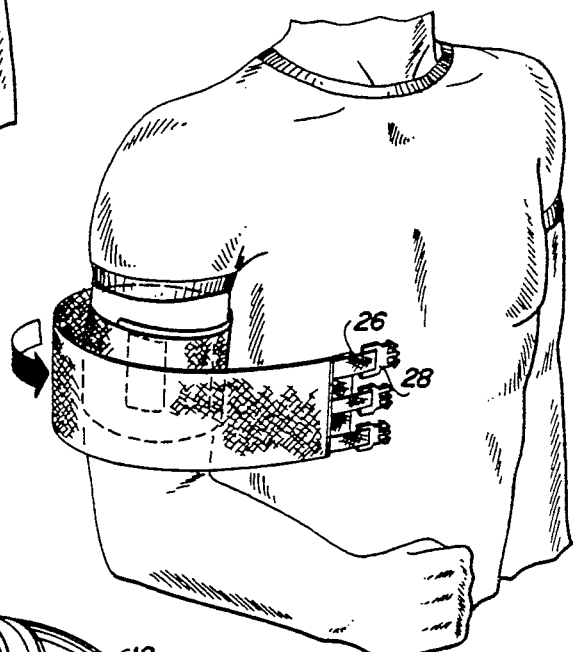

The function served by the engaging means is more clearly shown in FIGS. 4(a) and 4(b) wherein the wrapping about the upper arm is shown. In FIG. 4(a), a single wrap about the arm is shown made in an internal wrap wherein the wrap begins toward the axis of the body and continues around the back of the arm. The wrap has not been drawn tight to show the relative position of the engaging means. In the case of the single wrap as shown in FIG. 4(a), only one of the engaging means contacts the elastic member. In FIG. 4(b), the wearer has received a double internal wrap and the engaging means 21 and 22 provide a more secure wrap that is less likely to move during use. Normally, the wrap is made under some tension, but not enough to restrict blood flow in the arm of the user. In FIG. 4(b), it is to be noted that the second end 27 has been removed with the three release means being decoupled from their adjacent parts. This is to illustrate how readily the elastic member can be decoupled by use of the release means from the second end 27 and the shoulder pad assembly. This feature permits the wearer to be rewrapped without requiring other equipment to be removed.

Figure 4C:
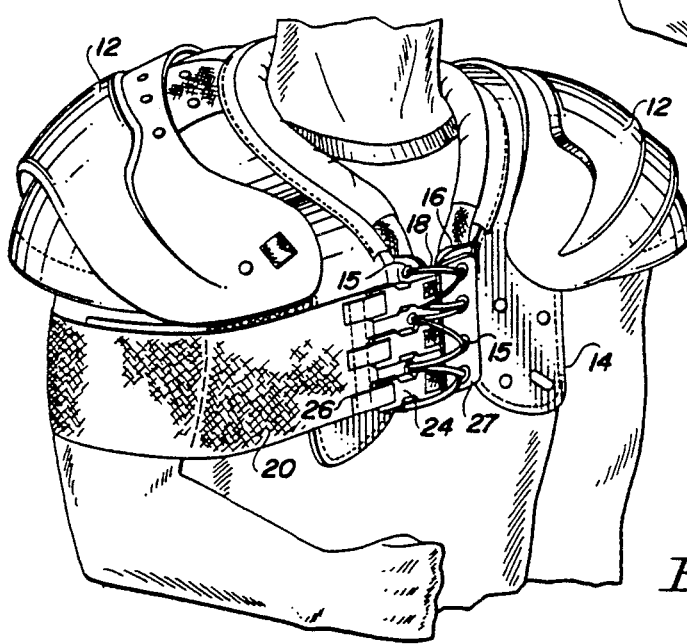
FIG. 4(c) shows the combination of the present invention with a conventional shoulder pad assembly positioned for use.

The affixation of the present invention to the shoulder pad assembly is shown in FIG. 4(c) wherein the elongated elastic member is shown wrapped about the upper arm in an internal rotation wrap below the protective extension 12 of the shoulder pad assembly. The elastic member 20 extends across the adjacent portion of the chest of the wearer and overlies the first frontal protector with the second end 27 being affixed to the opposing frontal protector by lashing 18 drawn through the grommets 15. The male portions 28 and female portions of the release means 24 are inserted and locked and the athletic brace is in position to both support the shoulder joint and protect against subluxation.

The movements of the upper arm 31 that are known to promote subluxation of the shoulder 32 are shown in FIG. 3 wherein the abductive movement of the arm upward and away from the central axis of the body is shown by the arrow. In addition, the external rotation or movement of the humerous in its socket outwardly away from the torso is shown by the circular arrow on the dashed line of the arm in its abducted position. The combination of these two movements greatly increases the tendency of the humerous to move out of the socket in the scapula. These partial dislocations are commonly referred to as subluxations and their repeated occurrences enhance the likelihood that they will recur.

When the wearer is provided with the present invention as shown in FIG. 4(c), the abductive movement away from the body and the external rotation both encounter the opposing or restoring force of the elastic member 20. Thus, the wearer is ever-conscious of the fact that there will be a movement limitation determined by the present invention. He is alerted to the fact that during competition, this limit is likely to be encountered. As he makes one or both of the two movements being controlled, the increasing resistance encountered from the elastic member should indicate to the athlete that he has to change his body position in order to complete his assigned task. The limits are established by the initial tension provided to the elastic member, by the position of the wrap on the upper arm and the number of turns thereof. The engaging means fixes the length of the elastic member once the wrap of the upper arm is made. In the event that there should be an adjustment necessary or replacement of the elastic member during competition, the athlete need not remove his shoulder pads. The release means 24 is provided to allow the elastic member to be detached, replaced or rewrapped as desired. Access to the assembly is provided merely by removal of the identifying shirt of the athlete.

The use of a flexible and accessible bracing system does not encumber the athlete as is the case with rigid brace assemblies or preventer staps worn with vests and the like. This invention is found to have been successful in decreasing the chances of subluxation, especially in the case of wide receivers in football. The present athletic brace is relatively inexpensive to manufacture and comfortable for the wearer. At the conclusion of the athletic activity, the wearer need only decouple the release means so that the wrap is separated from the second end 27. In practice, the second end 27 is left with the individual shoulder pad assembly. No assistance is necessary to remove the present invention from the wearer.

While the above description has referred to a particular embodiment of the invention, it is to be recognized that many modifications and variations may be made therein without departing from the scope of the invention as claimed.

I claim:

1. Apparatus to be used with an athletic shoulder pad assembly for reducing the possibility of a subluxation of the shoulder while permitting movement of the upper arm, said apparatus comprising:
    a) an elongated elastic member for wrapping about the upper arm, said member having first and second ends and length and width dimensions, said length being dimensioned to permit an internal wrapping of the upper arm;
    b) engaging means affixed to said elastic member proximate to the first end thereof for removably engaging an adjacent portion of the elastic member when said member is wrapped about the upper arm; and
    c) attachment means provided at the second end of said elastic member and including a plurality of spaced grommets for securing said second end to the assembly at a location inwardly spaced from the shoulder, the wrapping of said first end about the upper arm limiting abduction and rotation thereof and thereby reducing the possibility of subluxation of the shoulder.

2. The invention in accordance with claim 1 further comprising release means included in said elastic member between the first and second ends thereof for permitting a decoupling of the second end thereof.

3. The invention in accordance with claim 2 wherein said release means is located proximate to the second end of said elastic member thereby permitting said second end to remain secured to the assembly during periods of non-use.

4. The invention in accordance with claim 3 wherein the width dimension of the elastic member is substantially equal to the length of the upper arm of the wearer.

5. In combination with an athletic shoulder pad assembly of the type having adjacently spaced frontal protectors that are interlashed during use, a device for decreasing the tendency of a shoulder to subluxiate which comprises:
    a) an elongated elastic member having first and second opposing ends, said member being releasably secured at said second end to one of the frontal protectors, said member having a length dimension which permits wrapping the first end about the upper arm of the wearer;
    b) engaging means affixed to said elastic member proximate to said first end for removably engaging an adjacent surface of the elastic member when said member is wrapped about the upper arm; and
    c) release means included in the elastic member proximate to said second end thereof for permitting a decoupling of said end from the elastic member.

* * * * *